United States Patent [19]
Yu

[11] Patent Number: 5,917,029
[45] Date of Patent: Jun. 29, 1999

[54] SUGAR-RESPONSIVE ENHANCERS IN α-AMYLASE GENES

[75] Inventor: Su-May Yu, Taipei, Taiwan

[73] Assignee: National Science Council, Taipei, Taiwan

[21] Appl. No.: 09/038,227

[22] Filed: Mar. 11, 1998

[51] Int. Cl.$^6$ .................................................. C12N 15/11
[52] U.S. Cl. ............................................................ 536/24.1
[58] Field of Search ................................. 435/410, 320.1, 435/69.1; 536/24.1

[56] References Cited

U.S. PATENT DOCUMENTS 5,460,952  10/1995  Yu et al. ................................. 435/69.1

OTHER PUBLICATIONS

Chan et al., "Novel Gene Expression System for Plant Cells Based on Induction α–Amylase Promoter by Carbohydrate Starvation", The Journal of Biological Chemistry 269:17635–17641, 1994.

Chen et al., "Expression of α–amylases, Carbohydrate Metabolism, and Autophagy in Cultured Rice Cells is Coordinately Regulated by Sugar Nutrient", The Plant Journal 6:625–636, 1994.

Gallie et al., "The Regulation of Gene Expression in Transformed Maize Aleurone and Endosperm Protoplasts", Plant Physiol. 106:929–939, 1994.

Gubler et al., "Gibberellin–Responsive Elements in the Promoter of a Barley High–pI α–Amylast Gene", The Plant Cell 4:1435–1441, 1992.

Lanahan et al., "A Gibberellin Response Complex in Cereal α–Amylase Gene Promoters", The Plant Cell 4:203–211, 1992.

O'Neill et al., "The α–Amylase Genes in *Oryza sativa* Characterization of cDNA clones and mRNA Expression During Seed Germination", Mol. Gen. Genet 221:235–244, 1990.

Sheu et al., "Carbohydrate Starvation Stimulates Differential Expression of Rice α–Amylase Genes that is Modulated through Complicated Transcriptional . . . ", The Journal of Biological Chemistry 271:26998–27004, 1996.

Sheu et al., "Control of Transcription and mRNA Turnover as Mechanisms of Metabolic Repression of α–Amylase Gene Expression", The Plant Journal 5:655–664, 1994.

Tanida et al., "Functional Dissection of a Rice High–pI α–Amylase Gene Promoter", Mol. Gen. Genet. 244:127–134, 1994.

Huang et al, Nucleic Acids Research, vol. 18 (2): pp. 7007–7014, 1990.

*Primary Examiner*—Terry McKelvey
*Attorney, Agent, or Firm*—Fish & Richardson P.C.

[57] ABSTRACT

Sugar-responsive enhancers derived from cereal α-amylase genes. Also featured are expression vectors and other isolated DNA's containing such enhancers, as well as uses of the expression vectors.

5 Claims, 10 Drawing Sheets

```
                              -30       -20       -10        +1        10        20        30        40
                               .         .         .         .         .         .         .         .
αAmy3   TATATATGCCCCCGACGTCGAGGTCATTCGCCACGAACACATCGATCATCATCCATCATCTACAAGAGATCGATCAGTA  ---TO A

αAmy7   TATAAATACCTGACCAGACACACCCAGGAGCTTCATCAATCATCCATCTCCGAAGTGTCTGCAGCATGCAGGTGC      ---TO B

αAmy8   TATAAAATAGAGGCCAGTTCAGGCAATGCAAGAGCAAGAGAGTACAGCAGGCAGCTCTTCTCTCTTTGCGA          ---TO C 50        60        70        80        90
                    .         .         .         .         .
FROM A--- GTGGTTAGCAGCAACTCACTATGCGAACACGGTTTCAGCTTACACAGATATG   (SEQ ID NO. 4)

FROM B--- TGAACACCATGGTGAACAAACACTTCTTGTCC                       (SEQ ID NO. 5)

FROM C--- AGGTTGGCTACTTGGCCAGCCATTAGAAACAAGTTAGTTTGGAGAAGAAGCA   ----TO D 100       110       120       130       140       150
                    .         .         .         .         .         .
FROM D---- GAGTTGAGACTGCATTTGCATTGCTCTCTGTAGCCATGGGCCAAGCACCATGTCACCCTGTG  (SEQ ID NO. 6)
```

FIG. 1A

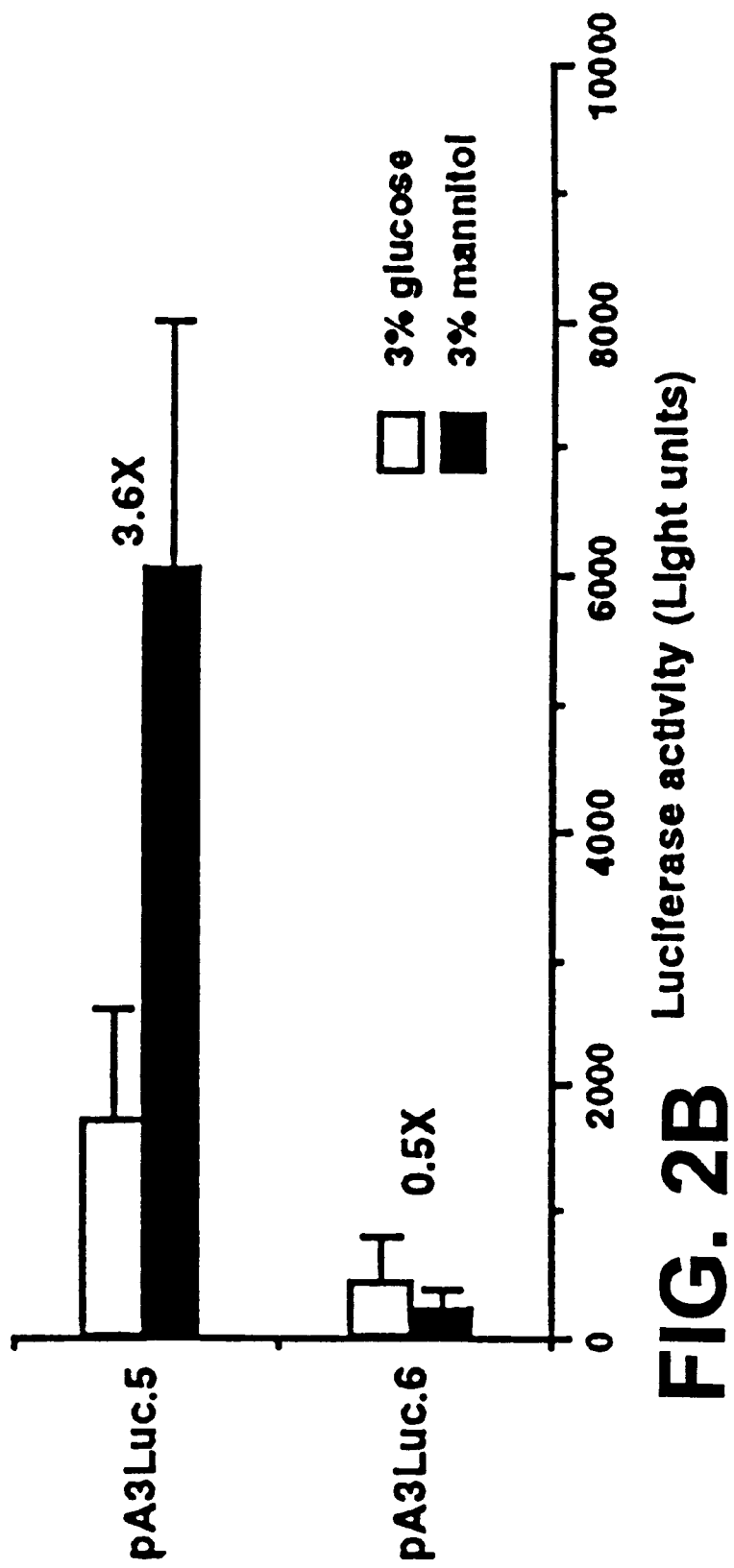

SUGAR-RESPONSIVE ENHANCERS IN α-AMYLASE GENES

FIELD OF THE INVENTION

This invention relates to transcription regulation of plant genes.

BACKGROUND OF THE INVENTION

Plant cell culture expression systems have several advantages over bacterial, yeast, or Baculoviral expression systems. Bacteria do not, and yeasts only limitedly, carry out post-translational modifications of the recombinant eukaryotic proteins they express. Such modifications are often necessary for the proper function of proteins. Baculovirus is a potent transformation vehicle for higher eukaryotes, and in general, proteins expressed by Baculoviral expression systems are properply modified. However, the cost for culturing Baculovirus is high. In addition, the host cells are eventually lysed by Baculovirus, resulting in the contamination of the expressed recombinant protein by thousands of host proteins released into the culture medium. Consequently, purification of the expressed recombinant protein may be rendered difficult.

Plant cells, on the other hand, are higher eukaryotic cells and thus able to perform sophisticated post-translational protein modifications of expressed eukaryotic proteins. Plant cells can also secrete the expressed proteins into culture media, making the purification of the proteins easier. Media for plant cell culture mainly contain salts and vitamins, and no serum supplement is required. Thus, the media cost much less than those used to culture insect cells which are used for the Baculovirus transfection.

Plant cell cultures are a potential commercial source of medicines, dyes, enzymes, flavoring agents and aromatic oils. Plant cell culture production of such components are sought when (1) they are naturally produced by plants in small quantities, or in fleeting or unharvestable developmental stages of the plants' life cycle; (2) they are produced by plants which are not amenable to agriculture or are native to vanishing or inaccessible environments; and (3) they cannot be satisfactorily synthesized in vitro.

Attempts to produce products by plant cell culture, however, are often commercially unsuccessful due to such factors as insufficient production or secretion of the desired product, poor cell growth, and difficulties in maintaining the appropriate cell type in culture.

The α-amylase expression system of rice callus has features that make it of potential use in plant cell fermentation technology. These features include high and sustained levels of expression, expression irrespective of either the tissue origin of the cell culture or tissue formation in the culture, and the ability to secrete the recombinant protein products.

α-amylases are the major amylolytic enzymes for hydrolysis of starch stored in the endosperm during germination of cereal grains. These enzymes catalyze the hydrolysis of α-1,4 linked glucose polymers. During the initial germinating period, cells in the aleurone layer of seeds synthesize α-amylases. Together with a-glucosidase and enzymes restricting dextrinase, the α-amylases are secreted into the endosperm and hydrolyze starch to form glucose and maltose, providing the nutrients needed for the growth of the germ (Rogers et al., J. Biol. Chem., 259:12234–12240, 1984; Rogers, J. Biol. Chem., 260:3731–3738, 1985).

Currently, 7 α-amylase cDNA's and 9 α-amylase genomic DNA groups have been cloned in barley (Chandler et al., Plant. Mol. Biol., 3:401–418, 1984; Deikman et al., Plant Physiol., 78:192–198, 1985; Krushseed et al., J. Biol. Chem., 263:18953–18960, 1988; Knox et al., Plant Molecular Biology, 9:3–17, 1987). The α-amylase genes of wheat are grouped into α-Amy1, α-Amy2, and α-Amy3. The proteins encoded by α-Amy1 and α-Amy2 have high and low isoelectric points, respectively, and these two gene groups each include more than 10 genes that are expressed in germinating seeds. The α-Amy3 gene group includes 3–4 genes, and they are expressed in immature seeds (Baulcombe et al., Mol Gen. Genet., 209:33–40, 1987).

Rice α-amylase isozymes are encoded by at least nine genes (Thomas et al., Plant Physiol., 106:1235–1239, 1994). Expression of α-amylase genes in rice has been found to be under different modes of tissue-specific regulation: in the embryo of germinating seeds and in suspension cultured cells, expression is activated by sugar deprivation and repressed by sugar provision (Karrer et al., Plant J., 2:517–523, 1992; Yu et al., J. Biol. Chem., 266:21131–21137, 1991; Yu et al., Gene, 122:247–253, 1992; and Yu et al., Plant Mol. Biol., 30:1277–1289, 1996). In the endosperm of germinating seeds, expression is activated by gibberellic acid and repressed by abscisic acid and osmotic stress (Itoh et al., Plant Physiol., 107:25–31, 1995; and Yu et al., Plant Mol. Biol., 30:1277–1289, 1996). Studies with rice suspension cells have shown that α-amylase expression, carbohydrate metabolism, and vascular autophagy are coordinately regulated by sucrose levels in the medium (Chen et al., Plant J., 6:625–636, 1994). Both the transcription rate and mRNA stability of α-amylase gene in cells increases in response to sucrose depletion in the culture medium (Sheu et al., Plant J., 5:655–664, 1994). Studies using transgenic rice carrying β-glucuronidase (GUS) gene under the transcriptional control of an α-amylase gene promoter proved that the regulation of α-amylase gene expression by sugars involves a transcriptional control mechanism (Chan et al., Plant Mol. Biol., 22:491–506, 1993; Chan et al., J. Biol. Chem., 269:17635–17641, 1994; and Huang et al., Plant Mol. Biol., 23:737–747, 1993). Sugar-dependent repression of α-amylase gene expression has also been observed in Aspergillus oryzae (Tonomura et al., Agric. Biol. Chem., 25:1–6, 1961) and Drosophila melanogaster (Benkel et al., Proc. Natl. Acad. Sci. USA, 84:1337–1339, 1987), and the mechanism was shown to involve transcriptional control (Magoulas et al., Genetics, 134:507–515, 1993; and Tsuchiya et al., Biosci. Biotech. Biochem., 56:1849–1853, 1992).

The synthesis of α-amylases and levels of their mRNA are greatly induced under sucrose starvation. An increase of α-amylase synthesis is assumed to accelerate hydrolysis of cellular starch as an energy source when exogenous carbon source is depleted. Under normal growth condition with an adequate supply of sugar, α-amylase is subjected to metabolite repression. It has been further observed that α-amylases synthesized by cultured rice cells are secreted into the culture medium and can account for about 15–20% of the total proteins present in the medium during periods of sugar depletion.

By using α-amylase gene-specific DNA fragments and nuclear run-on transcription analysis, transcription of eight α-amylase genes has been shown to increase in response to sucrose starvation (Sheu et al., J. Biol. Chem., 271:26998–27004, 1996). A positive correlation between the transcription rates and the steady-state mRNA levels suggests that transcription regulation plays an important role in the differential expression of individual α-amylase genes.

U.S. Pat. No. 5,460,952 discloses a gene expression system utilizing the transcriptional regulation characteristics of the α-amylase gene promoter regions. In this system, an α-amylase promoter controls the expression of foreign genes in transformed plant cells as well as the secretion of the foreign gene products into the medium.

SUMMARY OF THE INVENTION

The present invention is based on the discovery of sugar-responsive enhancer sequences within the α-amylase promoters. These sequences enhance sugar-induced gene expression, by, e.g., more than one fold, in a dose-dependent manner.

Accordingly, the invention features isolated DNA's containing two or more (e.g., 3, 4, 10, or any feasible number) copies of a sugar-responsive enhancer of a cereal α-amylase gene such as rice αAmy3. The enhancer is derived (i.e., isolated) from a promoter region of the cereal α-amylase gene. Examples of the enhancer include SEQ ID NOs:1, 2, and 3. The multiple copies of a given enhancer need not be placed in the same orientation in relation to each other.

Due to polymorphism that may exist at the α-amylase genetic locus, minor variations in the nucleotide sequence of a sugar-responsive enhancer may occur in any given cereal species. For purposes of this invention, as long as an adequate transcription-enhancing effect in response to sugar-starvation remains, enhancer sequences containing minor sequence variations as a result of natural polymorphism, or even as a result or recombinant genetic manipulation, are within the scope of this invention. In other words, the enhancer of the invention has a naturally occurring sequence, i.e, a sequence identical to that found in a naturally occurring α-amylase gene; or the enhancer is an active variant of the naturally occurring sequence.

An isolated (e.g., purified) DNA is a DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector, into an autonomously replicating plasmid or virus, or into the genomic DNA of a prokaryote or eukaryote; or which exists as separate molecule (e.g., a cDNA or a genomic DNA fragment produced by PCR or restriction endonuclease treatment) independent of other sequnces. It also includes a recombinant DNA which is part of a hybrid gene encoding additional polypeptide sequence.

The invention also features expression vectors that contain a promoter capable of directing expression of a coding sequence in an angiosperm cell, and a sugar-responsive enhancer (e.g, SEQ ID NO:1, 2, or 3) of a promoter region in a cereal α-amylase gene (i.e., rice αAmy3). In the vectors, the sugar-responsive enhancer is linked operably (either 5' or 3') to the promoter to enhance the transcriptional activity of the promoter in the absence of sugar. Also, the sugar-responsive enhancer in the vector is no longer linked, in the native (i.e., naturally occurring) configuration, to an α-amylase gene promoter region from which it is originally derived. In other words, the sugar-responsive enhancer is isolated from its cognate α-amylase gene. The enhancer can exist in one or multiple copies in the vectors and be placed in either orientation. An angiosperm cell is a monocotyledon, such as cereal (e.g., rice, barley, and wheat), or dicotyledon cell.

The promoter in the expression vectors can be a ubiquitously active one, such as one that is derived from an actin gene, cauliflower mosaic virus 35S ("CaMV35S") RNA or a ubiquitin gene, or an inducible one, such as one that is derived from an α-amylase (e.g., the rice αAmy3, αAmy6, αAmy7, αAmy8, or αAmy10 gene, which are also sugar-responsive; see U.S. Pat. No. 5,460,952), invertase, sucrose synthase, patatin, β-amylase, sporamin, or photosynthetic gene. Additional transcription regulatory elements such as other enhancers can also be included in the vectors.

The coding sequence can encode, for example, a polypeptide, or an antisense RNA that interferes with the function of another RNA (e.g., mRNA, transfer RNA, ribosomal RNA, and small nucleolar RNA).

The expression vectors can further comprise a signal-peptide-encoding sequence (e.g., one that is derived from a rice α-amylase gene) downstream of the promoter, so that the polypeptide products expressed from the expression vectors can be secreted by host cells.

To facilitate cloning, the expression vectors of the invention may comprise multiple restriction sites downstream of the promoter so that a coding sequence can be conveniently inserted into the vector downstream to the promoter. The sugar-responsive enhancer can be situated either upstream or downstream of the coding sequence.

The invention also features methods of producing a polypeptide in angiosperm cells. These methods utilize an expression construct containing a coding sequence for a polypeptide of interest, linked operably to a promoter capable of directing its expression in an angiosperm cell, and a sugar-responsive enhancer of a cereal α-amylase gene. Such a construct can be obtained by inserting the coding sequence into an expression vector of the invention. The construct and cells containing the construct are also within the scope of the invention.

In a method of the invention, appropriate angiosperm host cells are first transformed by the expression construct, and the transformed cells (including cells derived therefrom, e.g., through replication, regeneration, or differentiation) are then subjected to a sugar-free environment to promote expression of the polypeptide. A sugar can be sucrose, glucose, fructose, maltose, or any other polysaccharide that is metabolizable and provides a carbon source for cells.

A sugar-free (i.e., sugar-starved, or sugar-depleted) environment refers to an environment, e.g., aculture medium, that does not contain any sugar, or an environment whose sugar concentration is so low that it does not support the proliferation or respiration of cells. Occurrence of sugar starvation depends on multiple factors such as sugar concentration, the cell-to-medium volume ratio, and the length of incubation time in a medium.

The sugar-responsive enhancers of the invention that contain TATCCA can also enhance transcription in response to hormones such as gibberellic acid. Thus, in the above-described methods, cells tranformed with constructs containing such enhancers can be exposed to a giberellic acid-containing, instead of sugar-free, environment to promote production of the polypeptide. Germinating cereal seeds contain relatively high concentration of gibberellic acid. Thus, one can transform cells in a cereal seed with one such construct for producing a polypeptide of interest when the transformed seed germinates.

Of course, the above transformants can also be regenerated to tissue or even a whole plant (i.e., a transgenic plant) to promote expression of the polypeptide. Seeds of such a transgenic plant may also be germinated to promote expression of the recombinant polypeptide.

To facilitate recovery of the expressed polypeptide, a signal-peptide-encoding sequence can be integrated into the expression construct at an appropriate position, e.g., between the promoter and a coding sequence for the polypeptide. As a result, the polypeptide can be secreted to the medium of cultured cells or to the endosperm of germinating seeds, and thereby conveniently recovered.

Other features and advantages of the invention will be apparent from the following detailed description, and from the claims.

BRIEF DESCRIPTION OF THE DRAWINGS

FIG. 1A shows the nucleotide sequence comparison of the promoter regions (SEQ ID NOs:4–6) of rice αAmy3, αAmy7, and αAmy8.

FIG. 2B is a graph showing luciferase activity in transgenic tobacco suspension cells containing pA3Luc.5 and pA3Luc.6. Error bars indicate the standard error of luciferase activity from ten independent transgenic cell lines for each construct.

DETAILED DESCRIPTION OF THE INVENTION

Figure 1B:
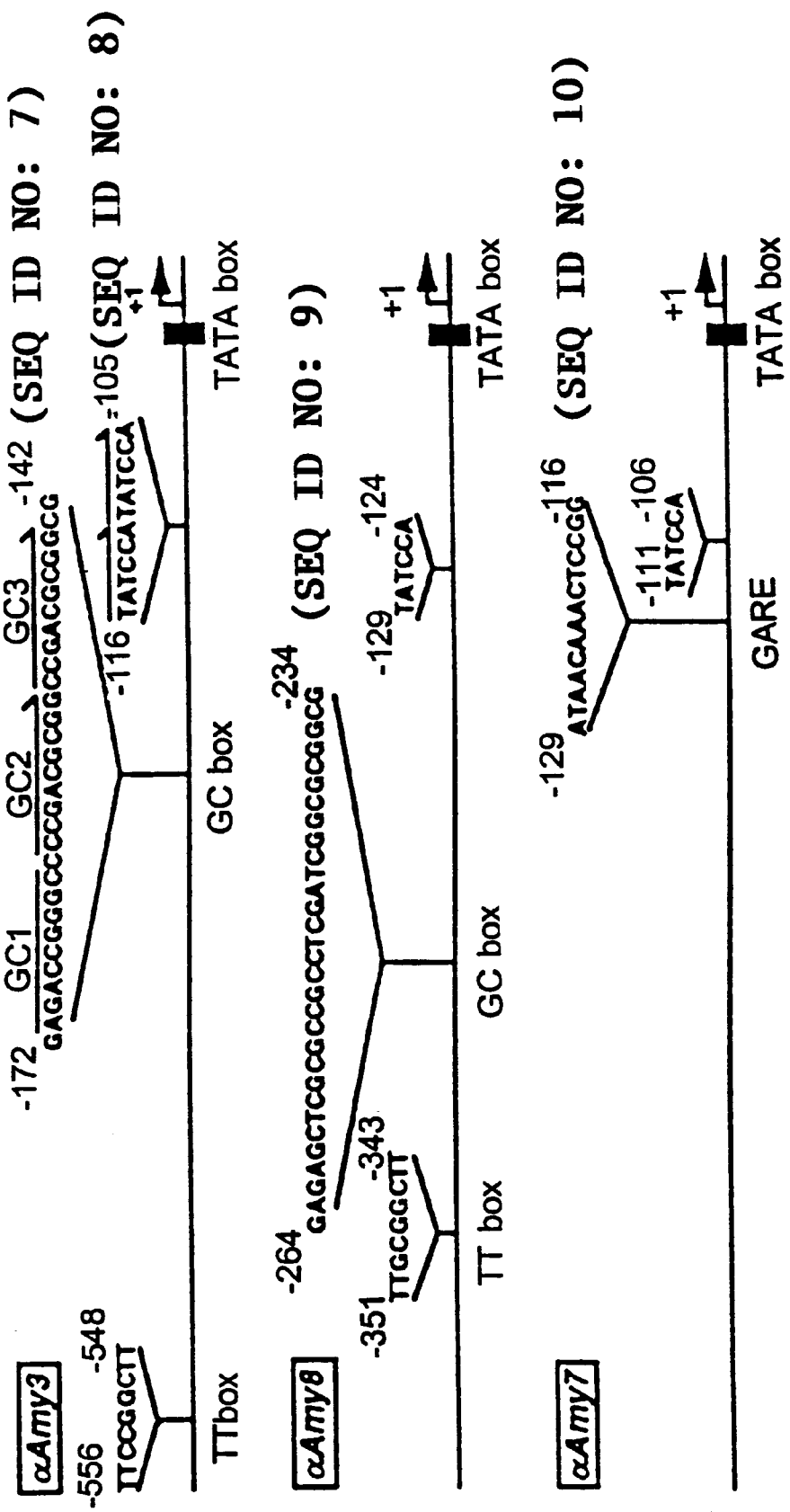
FIG. 1B is a schematic diagram showing the positions of various conserved motifs (SEQ ID NOs:7–10) in the promoter regions of rice αAmy3, αAmy7, and αAmy8.

Described below is the discovery of sugar-responsive enhancers in the promoter regions of cereal α-amylase genes. Furthermore, the efficiency of sugar starvation-induced transcription is found to increase linearly with the copy number of the enhancer inserted into a gene. Such enhancers can be used to enhance the expression of foreign genes in angiosperm cells that are exposed to a sugar-depleted or a gibberellic acid-containing environment.

The isolated DNA and expression vectors of the invention, which contain a sugar-responsive enhancer element of a cereal α-amylase gene, can be obtained by standard recombinant technology (see, e.g., Sambrook et al., Molecular Cloning, A Laboratory Manual, 2nd Ed., Cold Spring Harbor Press, Cold Spring Harbor, N.Y., 1989; and Ausubel et al., Current Protocols in Molecular Biology, Greene Publishing and Wiley-Interscience, New York, N.Y., 1993). For instance, a DNA fragment containing the enhancer is first obtained by polymerase chain reaction, using a rice α-amylase cDNA as a template. The fragment is then inserted into a plasmid that has already had an appropriate angiosperm promoter (or additionally, a coding sequence downstream of the promoter) in place.

Sugar-responsive enhancers from any cereal α-amylase gene can be identified by methods described in the Example below. Alternatively, one can identify such enhancers by searching for sequences in a cereal α-amylase promoter region that are homologous to the exemplary enhancer sequences described below; the sugar-responsiveness of the enhancers so identified can be confirmed with the assays described below. Indeed, homology exists among certain transcription regulatory regions of cereal α-amylase genes. For instance, examination of promoter sequences in eight rice, six barley, and five wheat α-amylase genes available in GENBANK reveals that all except four of these genes contain variants of the TATCCA element, and that most of the TATCCA elements/variants are located approximately 100 to 150 bp upstream of the transcription start sites. Recombinant variants of any naturally ocurring sugar-responsive enhancer sequences can be obtained by standard recombinant techniques such as mutagenesis.

Plant cells can be transfected with the isolated DNA or expression vectors using standard methods such as electroporation, particle bombardment, microinjection, ultrasonic method, polyethylene glycol-mediated protoplast transformation, poly-L ornithine method, calcium phosphate method, and Agrobacterium-mediated transformation system (see, e.g., U.S. Pat. No. 5,460,952, columns 17–18; and references in the patent).

Plant cells transformed by expression constructs (i.e, expression vectors containing a sequence encoding, e.g., a desired polypeptide), can be maintained and expanded in a sugar-free or $10^{-9} \sim 10^{-6}$M gibberellic acid-containing culture medium to promote expression of the polypeptide. The polypeptide can be subsequently extracted and purified from the cells using standard techniques. Alternatively, the polypeptide can be isolated from the culture medium if the expression constructs contain a signal peptide-encoding sequence so that the polypeptide is secreted into the medium (Chen et al., Plant J., 6:625–638, 1994; Sijmons et al., Bio/Technology, 8:217–221, 1990). One advantage of purifying proteins directly from a culture medium is that the amount of contaminant protein is substantially lower in culture media than in cell extracts.

Transformed plant cells can also be regenerated to transgenic tissue or a transgenic plant by well known techniques (see, e.g., Datta et al., Bio/Technology, 8:736–740, 1990; Peng et al., Plant Cell Reports, 9:168–172, 1990; Yang et al., Plant Cell Reports, 7:421–425, 1988; U.S. patent application Ser. Nos. 08/509,962 and 08/639,792). The recombinant polypeptide can then be recovered from the transgenic tissue or plant (or a part of the plant, such as its leaves, sheaths, stems, seeds, and roots, depending on the tissue-specificity of the promoter used).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, exemplary methods and materials are described below. All publications and other references mentioned herein are incorporated by reference in their entirety. Incase of conflict, the present specification, including definitions, will control. In addition, the materials, methods, and examples are illustrative only and not intended to be limiting.

The following data and protocols are used as examples to illustrate, but not limit, the isolated DNA's, expression vectors, constructs, and methods of the invention.

EXAMPLE

This Example describes the identification of several cis-acting sugar-responsive enhancer sequences in the rice αAmy3 promoter. Several transient expression systems were used in protoplasts prepared from rice suspension cells. By conducting loss-of-function, gain-of-function, and linker-scan mutation analyses, applicants have identified sugar-responsive enhancers that drive glucose starvation-induced gene expression at high levels. These sequences confer sugar responsiveness to a minimal promoter in an orientation-independent, yet dose-dependent manner. Three important motifs (i.e., the GC box, the G box, and the TATCCA element) that act synergistically in controlling αAmy3 expression were also identified. Finally, nuclear proteins from rice suspension cells were shown to bind to the TATCCA element in a sequence-specific and sugar-dependent manner.

Rice Cell Culture

Suspension cell cultures of rice (Oryza sativa cv. Tainan 5) were prepared as described previously (Yu et al.J. Biol. Chem. 266:21131–21137, 1991). Established suspension cells were subcultured every 7 days by transferring about 0.5 ml of cells into 25 ml of fresh liquid Murashige and Skoog ("MS") medium (Murashige and Skoog, 1962) containing 3% sucrose in a 125-ml flask. Cells were cultured on a reciprocal shaker at 120 rpm and incubated at 26° C. in the dark.

Primer Extension Analysis

Three gene-specific oligonucleotides that were 18–20 nucleotides in length and were respectively complementary to the signal peptide regions of rice αAmy7 and αAmy8, and the 5' untranslated leader of rice αAmy3 (FIG. 1B) were synthesized and used as primers. The primer extension analysis was performed according to Sutliff et al., Plant Mol. Biol., 16:579–591, 1991.

Plasmid Construction

A 1.7-kb SalI-EcoNI fragment from rice αAmy3 was blunt-ended and cloned into the ClaI site of pBSI-132, forming p3G-132II. This fragment contained the promoter region, the 5' untranslated sequence, and a 84 bp region downstream of the translation start site of rice αAmy3. pBSI-132 was generated by blunt-ended insertion of a PvuII fragment from pBSI (Chan et al., Plant Mol. Biol., 22:491–506, 1993) into the Hind III site of pTRA132 (Hayashimoto et al., Plant Physiol., 93:857–863, 1990). The PvuII fragment contained a β-glucuronidase ("Gus") coding sequence fused upstream to an Agrobacterium nopaline synthase ("Nos") gene terminator. pTRA132 is a plasmid containing, in this order, the cauliflower mosaic virus 35S RNA ("CaMV35S") promoter, a hygromycin B phosphotransferase ("hph") coding sequence, and the tumor morphology large gene ("tml") terminator.

Plasmid p3G-132II was used as the progenitor for all the constructs described in this Example. The oligonucleotide sequences used to prepare for the αAmy3 promoter constructs are listed in Table 1. Appropriate combination of 5' and 3' primers were used to generate various 5' deletions, internal deletions, or any other mutations by polymerase chain reaction ("PCR").

For 5' deletion constructs, the PCR products were digested with EcoRI and PstI and ligated into pBluescript KS+ (Stratagene) to generate p3.4, p3.5, and p3.6. These plasmids were digested with KpnI and PstI to release the promoter regions, which were then ligated into KpnI- and PstI-digsted pLuc, forming p3Luc.4, p3Luc.5, and p3Luc.6, respectively. pLuc was generated by insertion of a SalI-BglII fragment (which contained a luciferase ("Luc") coding sequence fused to a nos terminator) from pJD312 (Luehrsen et al., Meth. Enzymol., 216:397–414, 1992) into the SmaI site of pBluescript.

For internal deletion constructs, PCR was performed using the oligonucleotide-directed mutagenesis as described by Picard et al., Nucl. Acids. Res., 22:2587–2591, 1994. In this method, the 5' internal deletion primer were first paired with 3' primers to generate short DNA fragments by PCR. The PCR products then served as 5' primers and paired with same set of 3' primers to generate promoter fragments containing internal deletions. These promoter fragments were cloned into pLuc using the same procedures for constructing 5' deletions. The resultant plasmids were p3Luc.7, p3Luc.8, and p3Luc.9.

To prepare constructs for the gain-of-function analysis, a fragment containing a CaMV35S minimal promoter-alcohol dehydrogenase intron I (AdhI) was obtained by PCR using pJD312 as a template and inserted into the PstI and NcoI sites of pLuc to generate p35mALuc. DNA fragments containing various regions of the wild type or mutant αAmy3 promoters were PCR amplified, and cloned into pBluescript, generating p3.15 through p3.19 and p3.40. It seems that the manuscript is correct, since the construction of p3.4, which is a 5' deletion construct, has been described in the preceding page were generated. These plasmids were subsequently digested with XhoI and PstI, and the promoter regions thereby released were cloned into p35mALuc to generate p3Luc.15 through p3Luc.19 and p3Luc.40.

To generate plasmid p3Luc.18R, which contained SRS in the reverse orientation, p3Luc.18 containing SRS (−182 to −82) in the correct orientation was digested with XhoI and PstI, blunt-ended, and religated.

The −186 to −122 fragment in p3Luc.19 and the −133 to −82 fragment in p3Luc.40 were digested with XhoI and PstI and religated. Plasmids contain multiple copies of these fragments were thereby generated and designated as p3Luc.19x2 and p3Luc.41 through p3Luc.44. Mutation in the downstream or upstream copy of the duplicated TATCCA element in fragment −133 to −82 (p3Luc.41) was generated by using PCR-based oligonucleotide-directed mutagenesis (Picard et al., Nucl. Acids. Res., 22:2587–2591, 1994). The resulting constructs were designated as p3Luc.41m1 and p3Luc.41m2, respectively.

The linker-scan mutation of SRS was generated at 10-bp intervals by PCR-based oligonucleotide-directed mutagenesis using p3Luc.18 as a template. The mutated SRS fragments were digested with XhoI and PstI and cloned into p35mALuc to generate p3Luc.28 through p3Luc.36.

For construction of plasmids carrying SRS in the Act1 promoter, the Act1 5' region (including the 1.4-kb 5' flanking sequence, the 79-bp 5' noncoding exon, the 447-bp 5' intron, and the 25-bp first coding exon) was excised from pDM302 (Cao et al., 1992) with HindIII and subcloned into pBluescript. The EcoRI site in the multiple cloning sites of pbluescript was removed by digestion with EcoRV and XhoI and then blunt-ended and religated. The SRS sequence along with the 35S minimal promoter and part of the AdhI intron were excised with HindIII from p3Luc.18 and inserted into the HindIII site of pBluescript and generated p3.182. The SRS was excised with EcoRI from p3.182 and inserted into the EcoRI site (−459) of the Act1 promoter in pBluescript in one, two, or three copies and generated p3.37+, p3.37++, and p3.37+++. The three plasmids were then digested with SalI and PstI and the SRS-containing Act1 promoters were used to replace the 35S promoter and AdhI intron in pJD312 and generated p3Luc.37+, p3Luc37++, and p3Luc.37+++.

(Ou-Lee et al., 1986), re-suspended with the same buffer, and adjusted to $5 \times 10^6$ protoplast/ml.

Electroporation and Protoplast Culture

Plasmid DNA was transfected into rice protoplasts by electroporation. Each sample containing $2 \times 10^5$ protoplasts in 0.4 ml of electroporation buffer was mixed with 20 μg of test plasmid DNA, 5 μg of control plasmid DNA, and 50 μg of carrier (calf thymus) DNA[The underlined portion, which is taken from the manuscript, is missing in your draft.]. The mixture was transferred to a cuvette and placed in ice for 10 min. Electroporation was performed with an electrophorater (BTX) at 1000 V/cm, 400 μF, and 186 Ω. After

TABLE 1

Oligonucleotides Used in Making Promoter Constructs

| Oligo nucleide | Sequence | SEQ ID NO | Position | Constructs |
|---|---|---|---|---|
| a | ATCTTCAACCACCTGTGCTA | 25 | −87 −968 | p3Luc.3, p3AH, p 3Luc.7, p3Luc.8, p3Luc.9 |
| b | GTGGATAGAATTGCCATGT | 26 | −450 −432 | p3Luc.4 |
| c | AAATGGCTCGCCTTATCCA | 27 | −274 −256 | p3Luc.5, p3Luc.15, p3Luc.16, p3Luc.17 p3Luc.20, p3Luc.21, p3Luc.23, p3Luc.26 |
| d | ATTTATTGTGGTCGTCTCT | 28 | −100 −82 | p3Luc.6 |
| e | AATCTGTGTAAGCTGATTGGCA | 29 | +91 +71 | p3Luc.3, p3Luc.4, p3Luc.5, p3Luc.6, p3Luc.7, p3Luc.8, p3Luc9 |
| f | GTCGCCTTGG'ATTGCCTTATCCATA | 30 | −181 −172 −123 −109 | p3Luc.7 |
| g | GCCATGCTTT'TCTCCTGATCATTCT | 31 | −133 −124 −84 −70 | p3Luc.8 |
| h | TGTGGTCGTC'CGGTGTTCTATATAT | 32 | −94 −85 −41 −27 | p3Luc.9 |
| i | ATCCCGTCGCCTTGGAGA | 33 | −186 −169 | p3Luc.18, p3Luc.19 |
| j | AGAGACGACCACAATAAAT | 34 | −82 −120 | p3Luc.15, p3Luc.16, p3Luc.17, p3Luc.18, p3Luc.20, p3Luc.21, p3Luc.23, p3Luc.26 |
| k | ATAAAGCATGGCCACGTA | 35 | −122 −139 | p3Luc.19 |
| l | CCTCCATCCAagatgGtaccGGATAAGGCG | 36 | −237 −266 | p3Luc.16 |
| m | GCCTGAGGCatcatCTAgAGGtCTCCTCCT | 37 | −210 −239 | p3Luc.17 |
| n | AAGGCGACGGtgctatGcatCGTGATCGCG | 38 | −164 −203 | p3Luc.20 |
| o | CGGCCGCGTCtacaagCttaCTCCAAGGCG | 39 | −50 −179 | p3Luc.21, p3Luc.26 |
| p | TATTGCCTctcggATccagcCGCCATTTAT | 40 | −124 −95 | p3Luc.23, p3Luc.26 |
| L1 | CCCGGTCTCCAgaattcactGATGCGGCGG | 41 | −164 −193 | p3Luc.27 |
| L2 | CGCGTCGGGGatgaaTtcgtAAGGCGACGG | 42 | −154 −183 | p3Luc.28 |
| L3 | CCGCGTCGGCatgaattcacCCCGGTCTCC | 43 | −144 −173 | p3Luc.29 |
| L4 | CACGTAGGCGatGaaTtcgtCGCGTCGGGG | 44 | −134 −163 | p3Luc.30 |
| L5 | AAAGCCATGGCtggaattcatCCGCGTCGGC | 45 | −124 −153 | p3Luc.31 |
| L6 | ATAAGGCAATcggaatTctaCAACGTAGGCG | 46 | −114 −143 | p3Luc.32 |
| L7 | GTGGATATGGcggAattcgcAAAGCATGGC | 47 | −104 −133 | p3Luc.33 |
| L8 | AATAAATGGCcgaatTcctaATAAGGCAAT | 48 | −94 −123 | p3Luc.34 |
| L9 | AGACGACCACcgaAttctagGTGGATATGG | 49 | −84 −113 | p3Luc.35 |
| L10 | TGATCAGGAGctgaattCgtAATAAATGGC | 50 | −74 −103 | p3Luc.36 |
| q | TCACTCGAGGGCCATGCTTTATTGCCTT | 51 | −134 −116 | p3Luc.41 |
| r | TCCATCGATGCCATGCTTTATTGCCTT | 52 | −134 −116 | p3Luc.40 |
| s | GCCATCGATAGAGACGACCACAATAAA | 53 | −82 −99 | p3Luc.40 |

Protoplast Isolation

Three days after subculturing, a 25-ml suspension cell culture was transferred to a 9-cm petri dish. The MS medium was removed and cells were washed once with CPW7.4 buffer (2 mM KH2PO4, 1 mM KNO3, 10 mM CaCl2-2H2O, 1 mM $MgSO_4$-$7H_2O$, 1 μM KI, 0.16 μM $CuSO_4$-$5H_2O$, 5 mM MES, and 0.4M mannitol, pH 5.8) (Frearson et al., 1973). Cells were incubated with 15 ml of the protoplast isolation buffer (1% cellulase RS and 0.1% pectolyase Y-23 in CPW7.4 buffer) at 25° C. for 4 hr with shaking at 50 rpm. After cell wall digestion, protoplasts were filtered through a 33-μm nylon mesh (Small Parts, Inc.), washed three times with CPW7.4 buffer by centrifugation at 100×g for 5 min, and gently re-suspended in 2 ml of CPW7.4 buffer. The protoplasts were layered on 5 ml of 0.6M sucrose cushion in CPW7.4 buffer in a 15-ml conical tube, and centrifuged at 40×g for 10 min in a swing bucket rotor. Protoplasts on top of the sucrose cushion were collected and transferred to 10 ml of CPW7.4 buffer. The protoplasts were then washed electroporation buffer (0.14M NaCl, 2.7 mM KCl, 0.7 mM $KH_2PO_4$, 4.2 mM $Na_2HPO_4$, 5 mM $CaCl_2$, 0.4M mannitol)

electroporation, the protoplasts were kept on ice for 10 min, then mixed with 0.4 ml of electroporation buffer and 0.8 ml of 2× modified MS medium (containing 0.2 mg 2,4-D and 0.1 mg kinetin per liter) plus 400 mM glucose or 400 mM mannitol and 5 mM glucose. The protoplasts were plated in a 3-cm petri dish and cultured for 18 h at 26° C. in the dark.

GUS and Luciferase Assays

Protoplasts (2×106) were collected by centrifugation for 10 seconds at 12,000×g, re-suspended in 0.3 ml of an extraction buffer (100 mM K2HPO4, pH 7.8, 1 mM EDTA, 7 mM ɓ-mercaptoethanol, 1% Triton X-100, and 10% glycerol), and vortexed for 10 seconds at high speed. The disrupted protoplasts were centrifuged at 12,000×g and 4° C. for 5 min. Supernatant was collected and used for GUS or luciferase activity assay. The enzymatic activities of the cell extract maintain stable for at least one month at −80° C.

The fluorogenic assay for GUS activity was performed with modification of a method described by Jefferson, Plant. Mol. Biol. Reptr., 5:387–405, 1987. For each assay, 100 μl of 2× GUS assay buffer [100 mM NaPO4, pH 7, 10 mM ɓ-mercaptomethanol, 20 mM Na2-EDTA, 0.2% (w/w)

sodium laurylsarcosine, 0.25% (v/v) Triton X-100, and 1.8 mM 4-methylumbelliferyl β-D-glucuronide (MUG)] was dispensed into a 1.5-ml eppendorf tube. One hundred μl of cell extract was added and incubated at 37° C. in the dark for various lengths of time. Fifty μl of the reaction mixture was dispensed into 1,950 μl of 0.2 $Na_2CO_3$ immediately (t=0 min) and repeated after 120 min. Fluorescence (excitation at 365 nm and emission at 455 nm) was detected using a TKO 100 fluorometer (Hofer).

For luciferase assays, 50 μl of cell extract was placed n a luminometer cuvette (Sarstedt), and then 180 μl of luciferase assay buffer (25 mM Tricine, pH 7.8, 15 mM potassium phosphate, pH 7.8, 15 mM $MgSO_4$, 4 mM EGTA, 2 mM ATP, and 1 mM DTT) was added. The mixture was allowed to equilibrate to room temperature for about 15 min. Placing the cuvette in the counting chamber of a luminometer (LUMAT, Berthold) automatically activated the machine and 50 μl of 250 μM luciferin (Promega) was injected into the cuvette to start the reaction. The photons emitted were integrated over a 20-sec period and were expressed as light units (RLU)/20 sec.

Plasmid pUGI containing the ubiquitin promoter-GUS gene fusion was served as an internal standard. PUGI was generated by insertion of the BamHI-HindIII fragment [ubiquitin (ubi) promoter] from pAHC18 (Bruce et al., Proc. Natl. Acad. Sci. USA, 86:9692–9696, 1989) into pBSI digested with the same enzymes. Expression from the ubiquitin promoter was reduced less than 2-fold by glucose starvation of protoplasts. The GUS activity expressed from pUGI was used to standardize luciferase activity in cell extracts from cells grown with or without glucose.

Transformation of Tobacco

DNA fragments containing the αAmy3-Luc-Nos chimeric gene were excised from plasmids p3Luc.5 and p3Luc.6 with KpnI and SpeI and ligated into the KpnI and XbaI sites of pBIN19 (Bevan, Nucl. Acids. Res., 12:8711–8721, 1984) to generate pA3Luc.5 and pA3Luc.6. pA3Luc.5 and pA3Luc.6 were transferred into Agrobacterium tumefaciens strain EHA105 using an electroporation method described in the manufacturer's instruction manual for the electroporator BTX or using a freeze-thaw method (Holster et al., Mol. Gen. Genet., 163:181–187, 1984). The tabacco variety Nicotiana tabacum L. cv. Petit Havans SRI was used in this study. ransgenic tobacco cell lines were obtained by transformation of leaf discs with Agrobacterium according tothe method of Horsch et al., Plant Molecular Biology Manual, S. B. Gelvin and R. A. Schilperoot, eds, pp. A5:1–9, 1988. Suspension cell cultures of the transgenic tobacco were propagated as previously described (Yu et al., J. Biol. Chem., 266:21131–21137, 1991; and U.S. Pat. No. 5,460,952). Luciferase activity in the transgenic tobacco suspension cells was examined after the cells were growth in the presence or absence of sugar for 2 days.

Preparation of Nuclear Extract

About 5 g (fresh weight) of rice suspension cells grown in the presence or absence of sucrose were pulverized in liquid nitrogen and homogenized in 200 ml of homogenization buffer (400 mM mannitol, 50 mM Tris-HCl, pH 7.9, 5 mM $MgCl_2$, 1 mM EDTA, 0.1% BSA, 0.1% NP-40, 5 mM DTT and 1 mM PMSF). After this step, preparation of nuclear extract followed the procedures described by Mitsunaga et al., Nucl. Acids. Res., 22:1948–1953, 1994.

Gel Mobility Shift Assay

Oligonucleotides F1 through F5 were synthesized and their sequences are shown in FIG. 7A. F2 used as probe was prepared by phosphorylation of the 5' hydroxyl terminal with T4 polynucleotide kinase and $\gamma$-$^{32}$P-ATP (5000 Ci/mmol). DNA-protein binding reaction was carried out by incubation of 0.02 ng of labeled F2 with 20 μg nuclear extract in 20 μl of a solution containing 17 mM Hepes, pH 7.9, 60 mM KCl, 7.5 mM $MgCl_2$, 0.12 mM EDTA, 17% glycerol, 1.2 mM DTT, 0.5 μg poly(dI-dC) (Pharmacia), and 3 or 10 ng (150- or 500-fold amount of probe, respectively) competitor DNA. The assay mixture was incubated for 20 min at room temperature. After this step, electrophoresis of the assay mixtures and autoradiography of gel followed the procedures described by Mitsunaga et al., Nucl. Acids. Res., 22:1948–1953, 1994.

RESULTS (1) Sequence Analysis of the α-amylase Gene Promoters

Although the promoter regions of αAmy3 (Ramy3D) (Huang et al., Plant Mol. Biol., 23:737–747, 1993), αAmy7 (Ramy1A) (Itoh et al., Plant Physiol., 107:25–31, 1995), and αAmy8 (Ramy3E) (Chan et al., Plant Mol. Biol., 22:491–506, 1993; Chan et al., J. Biol. Chem., 269:17635–17641, 1994) have been shown to mediate sugar or hormonal regulation of GUS reporter gene expression in transgenic rice, the transcription start sites of these α-amylase genes have not been mapped precisely. Here the transcription start site of αAmy3 was mapped 28 bp, and those of αAmy7 and αAmy8 were mapped 29 bp, downstream of the TATA box and designated as +1 (FIG. 1A). Inspection of the promoter regions reveals two conserved sequence elements of 10 bp (TT box) and 31 bp (GC box) (Huang et al., Nucl. Acids. Res., 18:7007–7014, 1990b) that are present in the αAmy3 and αAmy8 promoters but not in the αAmy7 promoter (FIG. 1B). The GA response element (GARE) (Gubler and Jacobsen, 1992; Rogers et al., 1994) is present in the αAmy7, but not in the αAmy3 and αAmy8 promoters. A G box sequence (containing ACGT core) is located between nucleotides −141 and −132 of the αAmy3 promoter and between nucleotides −334 and −325 of the αAmy8 promoter. G box is present in the promoters of a variety of genes that are responsive to several environmental and physiological cues (Devetten et al., Int. J. Biochem., 26:1055–1068, 1994). Another sequence of 6 bp (TATCCA element) is present in two copies in the αAmy3 promoter but only in one copy in the αAmy7 and αAmy8 promoters. The functions of these elements in the sugar-dependent regulation of α-amylase gene expression have not been previously determined. The αAmy3 promoter is chosen here as a model for the following studies.

(2) Deletion Analysis of the αAmy3 Promoter

Figure 2A:
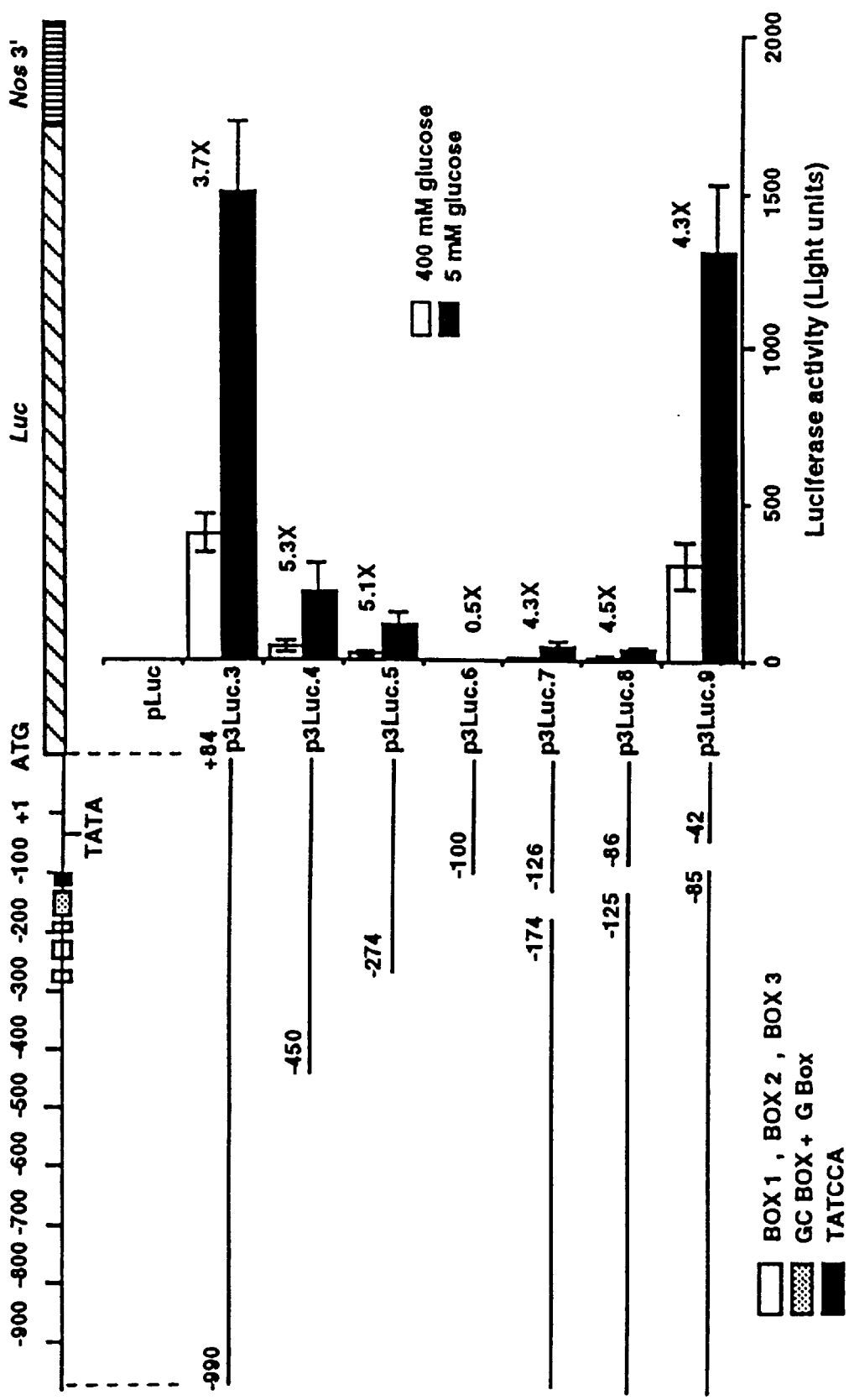
FIG. 2A is a graph showing luciferase activity in rice protoplasts transformed with expression constructs that contain various deletions in the rice αAmy3 promoter. Each of these plasmids was cotransfected with pUGI into rice protoplasts. Error bars indicate the standard error of three replicates for each construct. "X" indicates fold increase.

A DNA construct (p3Luc.3) containing the 1-kb promoter region (900-bp promoter plus 91-bp untranslated sequences) of the αAmy3 gene fused to the coding region of a luciferase gene was made (FIG. 2A). This construct was stably transfected into rice suspension cells and found to confer sugar-dependent repression of luciferase expression. In order to identify the sequences in the αAmy3 promoter that are involved in the sugar-dependent regulation, three constructs (p3Luc.4, p3Luc.5, and p3Luc.6) containing progressive deletions at the 5' end of the αAmy3 promoter were made (FIG. 2A). The resultant constructs were analyzed by transient expression in rice protoplasts.

Applicants found that 5 mM glucose can cause starvation of rice protoplasts and 400 mM glucose is normally required to maintain the osmolarity of rice protoplasts. Thus, after transfection, the protoplasts were analyzed in a medium containing 5 mM glucose plus 400 mM mannitol (starved) or containing 400 mM glucose (non-starved). The results show that, when a deletion of the αAmy3 promoter was made to nucleotide position −450 upstream of the transcription start site (p3Luc.4), the level of glucose starvation-induced luciferase expression dropped dramatically. The expression was further reduced when the deletion was made to position −274 (p3Luc.5). Despite the dramatic reduction in the absolute level of expression caused by the two promoter deletions, the fold induction of expression by glucose starvation was maintained at a similar level. Deletion of the next 174 bp (to position −100) (p3Luc.6) abolished luciferase expression regardless of the concentration of glucose.

Fragments from p3Luc.5 and p3Luc.6 that contain the luciferase coding sequence fused to the 274-bp and 100-bp αAmy3 promoter regions, respectively, were subcloned into binary vectors and transfected into tobacco via the Agrobacterium-mediated transformation. The independent transgenic tobacco plants for each construct was used to generate suspension cell cultures and luciferase expression in the culture cells was analyzed. As shown in FIG. 2B, the 274-bp promoter (pA3Luc.5) conferred glucose starvation-induced expression of luciferase, whereas the 100-bp promoter (pA3Luc.6) abolished the expression regardless of the concentration of glucose. Results shown in FIGS. 2A and 2B suggest that the cis-element(s) required for sugar-dependent regulation is located within the region between nucleotides $_b$274 and $_b$100 of the αAmy3 promoter.

Because the conserved GC box, G box, and TATCCA element were located between nucleotides −172 and −105 of the αAmy3 promoter (FIG. 1B), three constructs containing internal deletions between nucleotides −174 to −42 were made (FIG. 2A). A deletion from nucleotides −174 to −126 (including the GC box and G box) (p3Luc.7), or from −125 to −86 (including the TATCCA element) (p3Luc.8) led to a drastic decrease in the absolute level of luciferase activity but still conferred glucose response. Surprisingly, deletion from nucleotides −85 to −42 (p3Luc.9) restored the glucose-dependent luciferase expression to a level similar to that of the full length promoter (p3Luc.3). The above deletion analyses indicate that the promoter regions between nucleotides −990 and −450 and between nucleotides −274 and −86 are required for high level glucose starvation-induced expression of the αAmy3 promoter.

(3) Functional Analysis of the Sugar Response Sequence in the αAmy3 Promoter

Figure 3:
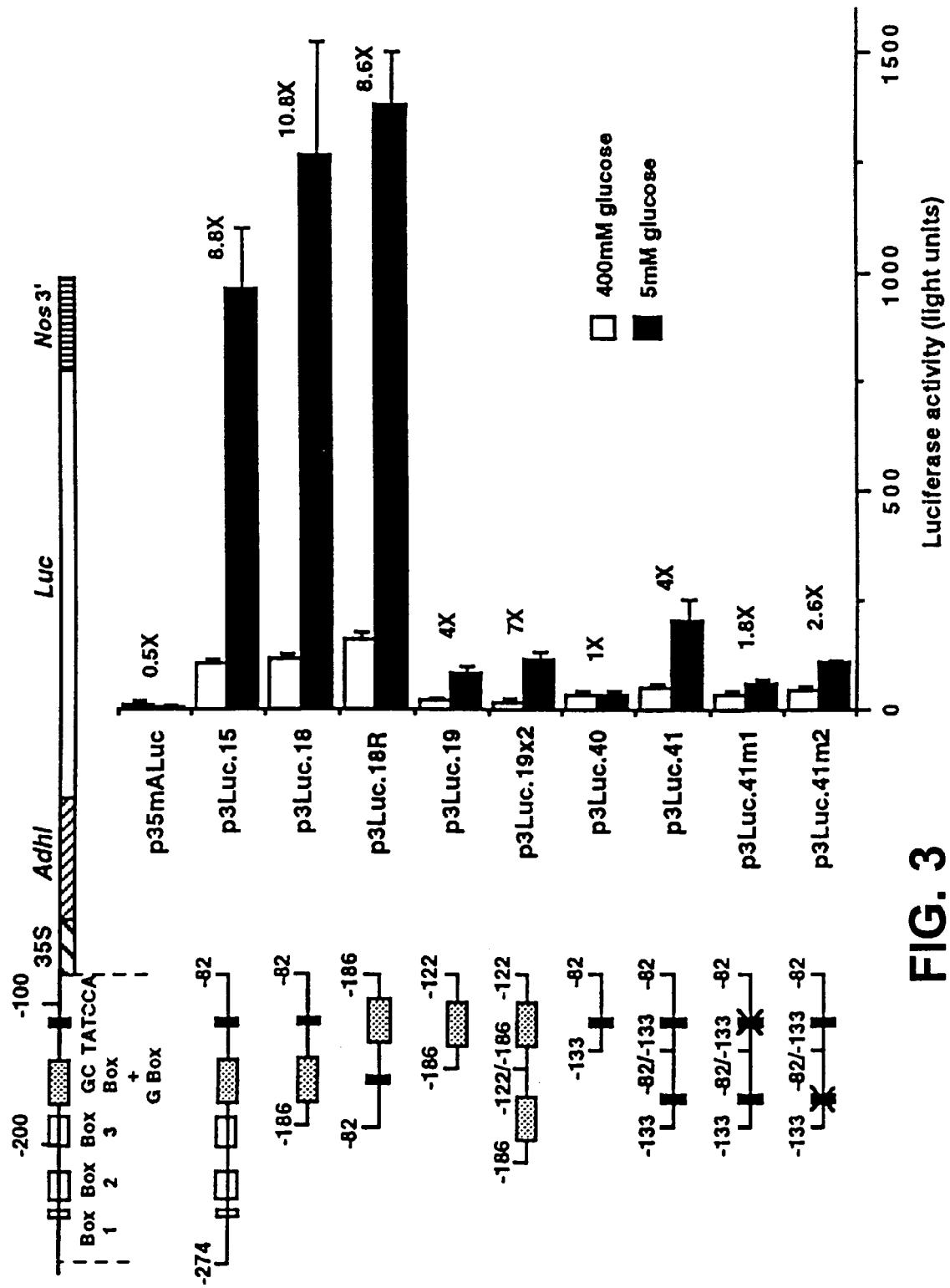
FIG. 3 is a diagram showing results from a functional analysis which identifies sugar-responsive sequences that confer glucose starvation inducibility to a minimal promoter. Various motifs such as the G box, the GC box, and the TATCCA element are indicated in the diagram.

To determine whether the cis-acting element(s) required for sugar-dependent regulation is located within the region downstream of nucleotide −274 in the αAmy3 promoter, fragments covering various regions between nucleotides −274 and −82 were inserted upstream of a CaMV35S (i.e., cauliflower mosaic virus 35S RNA) minimal promoter-AdhI-Luc fusion gene (supra), as shown in FIG. 3. The resultant constructs were tested for transcriptional activity in rice protoplasts. Expression of the basic construct containing no αAmy3 promoter sequence (p35mALuc) did not respond to glucose starvation. When the fragment containing nucleotides −274 to −82 (p3Luc.15) or nucleotides $_b$186 to $_b$82 (p3Luc.18) was fused upstream to the 35S minimal promoter, a high level of glucose starvation-induced expression of luciferase was observed. The region between nucleotides −274 and −176 in the αAmy3 promoter contains three protein-binding sequences, designated Box 1, Box 2 and Box 3, respectively (Mitsunaga et al., Nucl. Acids. Res., 22:1948–1953, 1994). The three boxes each contain a conserved GCCG G/C CG motif, and they have been proposed to be involved in sugar-dependent regulation of the αAmy3 promoter (Mitsunaga et al., Nucl. Acids. Res., 22:1948–1953, 1994). Deletion of the promoter region containing the three boxes (p3Luc.18) resulted in a 30% increase of glucose starvation-induced expression, suggesting that this region may contain negative cis-acting elements. Surprisingly, when the fragment containing nucleotides −186 to −82 ("fragment −186 to −82") was inserted in reverse orientation upstream of the 35S minimal promoter (p3Luc.18R), expression of luciferase in response to glucose starvation was as high as that with the promoter fragment inserted in the correct orientation (p3Luc.18). These results demonstrate that the region between nucleotides −186 and −82 contains most, if not all, of the cis-acting element(s) required for conferring a high level of glucose starvation-induced expression under the 35S minimal promoter. This region is designated as a sugar-response sequence ("SRS").

One copy of fragment $_b$186 to $_b$122 (p3Luc.19), which contains the GC box and G box, caused significant reduction in expression, but still conferred glucose response. Two copies of fragment −186 to −122 (p3Luc.19x2) increased the expression in response to glucose starvation. One copy of fragment −133 to −82 (p3Luc.40), which contains the duplicated TATCCA element, slightly elevated the expression of luciferase as compared with the control (p35mAluc), but conferred no glucose response. Interestingly, when this fragment was repeated in tandem (p3Luc.41), glucose response was restored and the absolute level of luciferase activity was higher than that of the promoter containing the GC and G boxes (p3Luc.19 or p3Luc.19x2). To examine whether the sequence or position of the TATCCA element relative to the TATA box is important, mutations in the duplicated TATCCA elements were generated. Results showed that mutations in either the downstream (p3Luc.41m1) or the upstream (p3Luc.41m2) copy of the duplicated TATCCA element reduced the expression.

Figure 4:
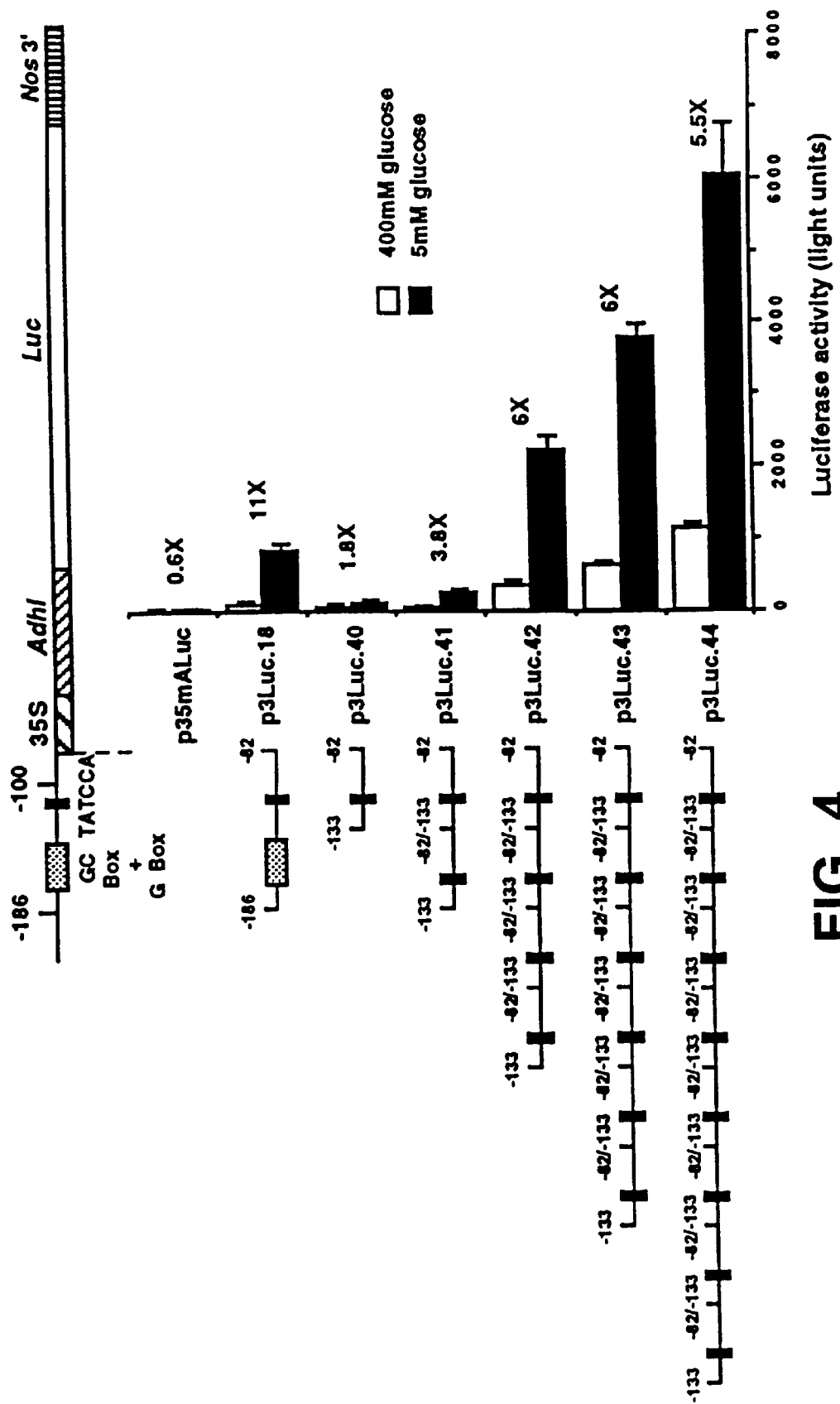
FIG. 4 is a diagram showing the sugar-dependent transcription enhancement effect of SEQ ID NO:3, which corresponds to nucleotides –133 to –82 of the rice αAmy3 promoter region. Some of the constructs contain tandemized copies of SEQ ID NO:3.

(4) A 52-bp Fragment Containing the TATCCA Element Enhances Transcriptional Activity Comparison of the luciferase activity produced by p3Luc.40 and p3Luc.41 in FIG. 3 suggests that the 52-bp fragment encompassing nucleotides −133 to −82 enhances transcription. Mutation in the TATCCA element within this fragment reduced transcription, confirming that the TATCCA element is essential for enhancing transcription. To further demonstrate the function of the element in enhancing transcription, multiple copies of the 52-bp fragment were fused upstream to the 35S minimal promoter, and the luciferase activity was assayed. As shown in FIG. 4, duplication of the 52-bp fragment resulted in the increase in the starvation-induced luciferase activity. The increase became almost linear as more copies of the fragment were added. Luciferase activity in non-starved cells also increased linearly with additional copies the 52-bp fragment, and consequently, the fold induction of the luciferase activity by glucose starvation was not parallelly increased. The results suggest that the 52-bp fragment enhances transcription of the minimal promoter regardless of the glucose concentration.

(5) SRS Acts as a Transcriptional Enhancer in a Sugar Insensitive Promoter

Figure 5:
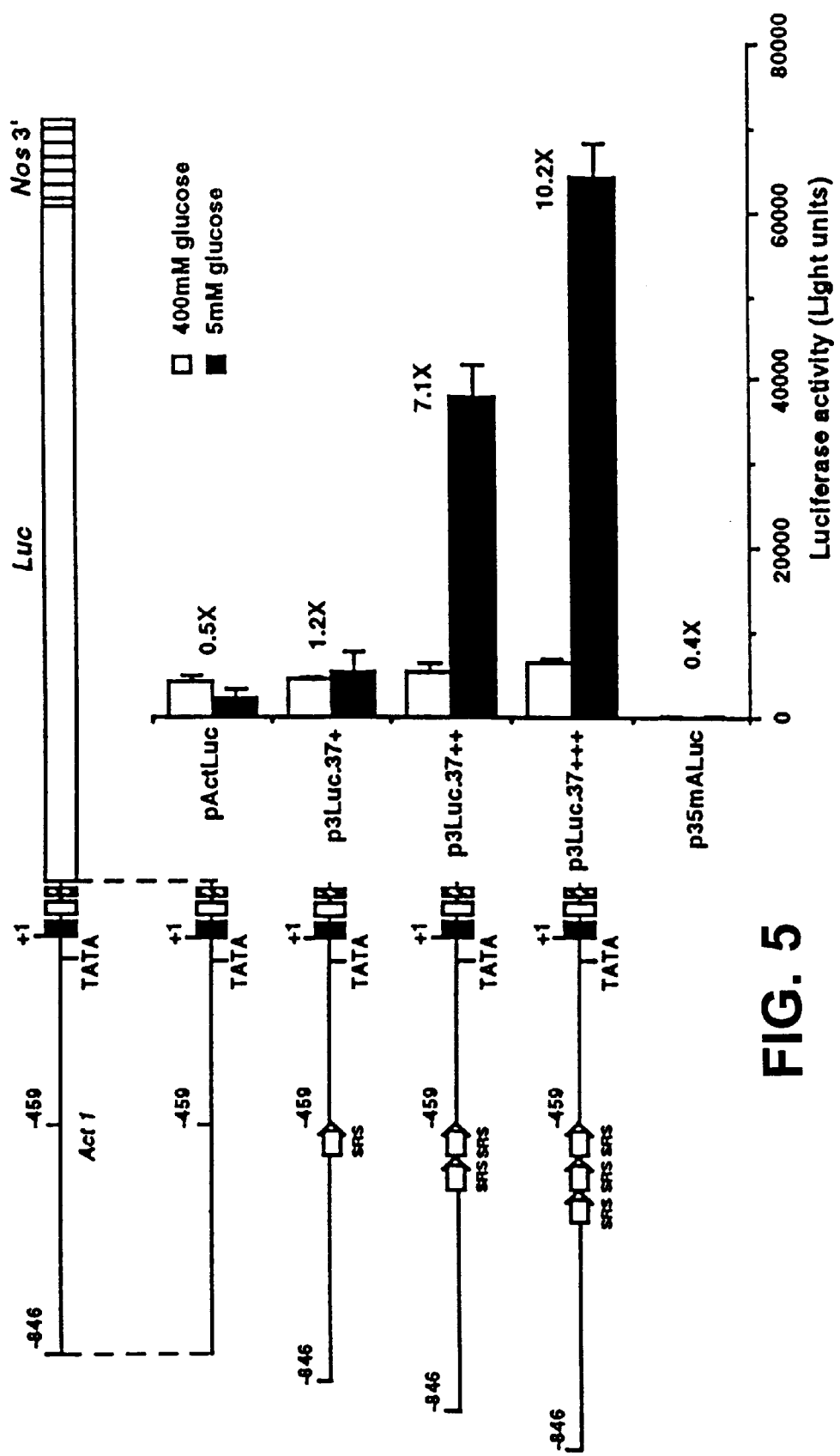
FIG. 5 is a diagram showing that SRS (i.e., SEQ ID NO:1) converts the sugar-up-regulated Act1 promoter into a sugar-down-regulated promoter. The constructs tested contain one to three copies of SRS.

The SRS conferred a high level of glucose starvation-induced expression under the 35S minimal promoter in an orientation-independent manner, suggesting that it may function as a transcriptional enhancer. To confirm this, the SRS was inserted in one, two, and three tandem copies at the EcoRI site (−459 bp upstream of the transcription start site) of the rice Act1 promoter (McElroy et al., Plant Cell, 2:163–171, 1990). The wild type and the SRS-containing Act1 promoters were fused upstream to the Luc gene as shown in FIG. 5. These constructs were then tested for transcriptional activity in rice protoplasts. Luciferase expression from the control construct (p35mALuc) was not detected. At high glucose concentrations, luciferase expression under the wild type Act1 promoter (pActLuc) was similar to that under the Act1 promoter containing one to three SRS copies. In glucose-starved cells, expression under the Act1 promoter containing one SRS copy (p3Luc.37+) increased 2-fold as compared with that under the wild type Act1 promoter. Surprisingly, duplication of SRS (p3Luc.37++) dramatically increased the fold induction by glucose starvation, and the fold induction increased almost linearly as more copies of SRS were dded (p3Luc.37+++). These results demonstrate that expression of luciferase under the Act1 promoter becomes inducible by glucose starvation if the promoter contains multiplecopies of SRS.

(6) Linker-Scan Mutation Analysis of SRS in the αAmy3 Promoter

Figure 6A:
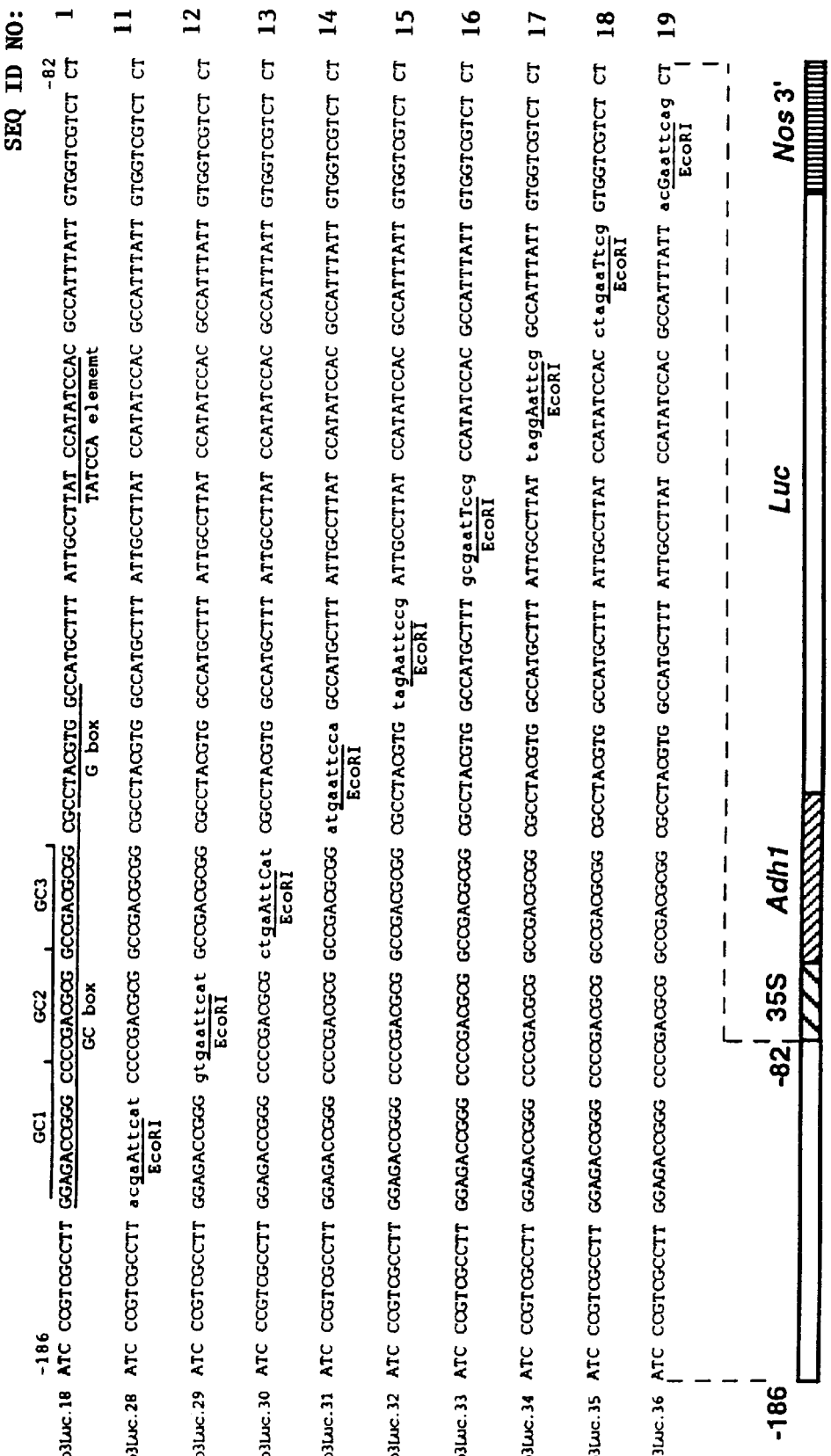
FIG. 6A shows the sequences (SEQ ID NOs:1 and 11–19) of SRS that contain various linker-scan mutations. The top sequence is wild type.

Understanding that SRS confers a high level of glucose starvation-induced expression under the Act1 and 35S minimal promoters, the next step was to more precisely locate the cis-acting elements involved in sugar responsiveness. Various 10-bp fragments containing EcoRI site (GAATTC) were introduced into p3Luc.18 individually to replace various regions within the SRS, thereby generating constructs p3Luc.28 through p3Luc.36, as shown in FIG. 6A. These constructs were then tested for luciferase expression.

Figure 6B:
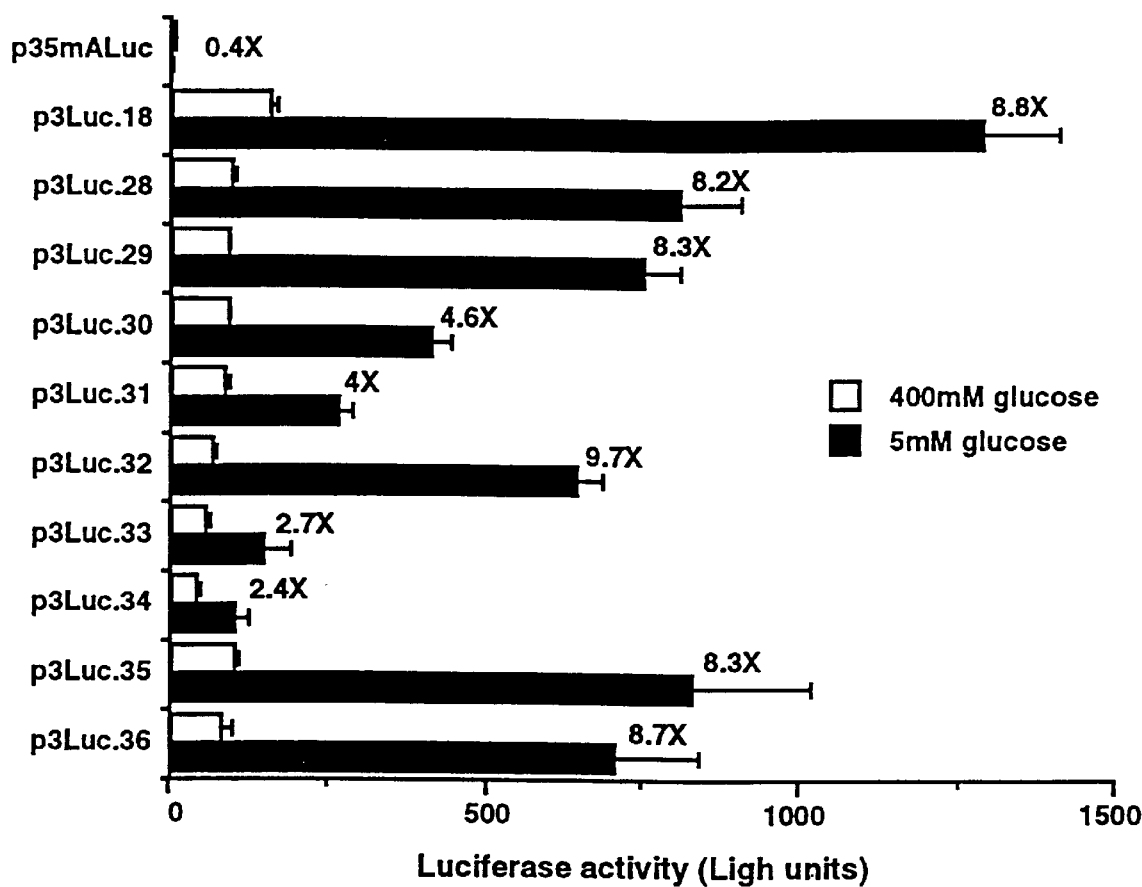
FIG. 6B is a diagram showing luciferase activity in rice protoplasts transformed with expression constructs containing SRS or a mutant thereof.

As shown in FIG. 6B, all the linker substitutions in the SRS had effects on luciferase expression. The GC box can be divided into three GC-rich subdomains designated GC1, GC2, and GC3 boxes, respectively. The GC2 and GC3 boxes each contain an identical 9-bp sequence CCGACGCGG. Mutations in the GC2 box (p3Luc.29) and the GC3 box (p3Luc.30) resulted in 40% and 60% reduction of expression, respectively, as compared to expression regulated by the wild type SRS sequence. Each of the two linker substitutions in the duplicated TATCCA element (p3Luc.33 and p3Luc.34) caused dramatic reduction in the level of glucose starvation-induced expression to 12% and 8% of the control (p3Luc.18), respectively. Mutations in the G box (p3Luc.31) resulted in an 80% reduction of expression. These results demonstrate that all of the sequences within SRS are necessary, and that the GC3 box, the G box, and the TATCCA element are the most important sequences for high level induction of gene transcription by glucose.

(7) Nuclear Proteins Binding to the cis-Acting Elements in SRS

Figure 7:
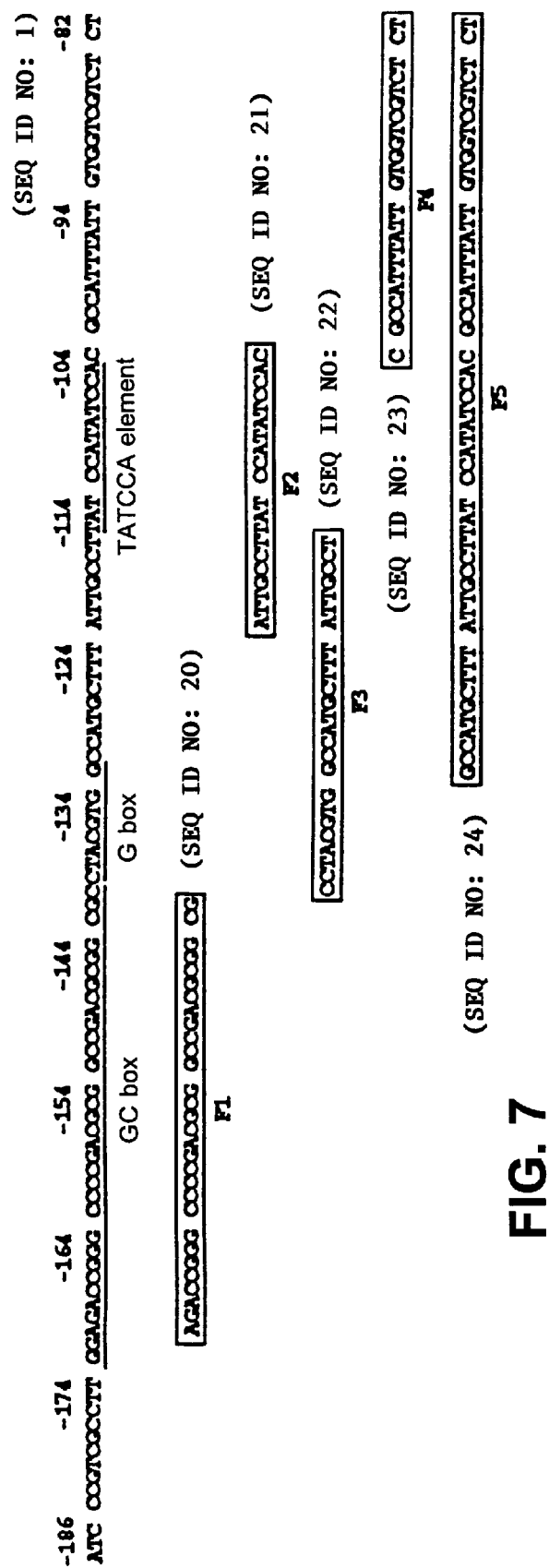
FIG. 7 shows the sequence and positions of several synthetic oligonucleotides (SEQ ID NOs:20–24) within SRS (SEQ ID NO:1) that were used for gel mobility shift assay.

Since the 52-bp fragment containing the TATCCA element enhanced glucose starvation-induced transcriptional activity (FIG. 4) and the TATCCA element is essential for conferring sugar-dependent regulation (FIG. 5), whether or not the nuclear proteins from rice suspension cells bind to the TATCCA element was examined. DNA fragments encompassing various SRS regions were synthesized and designated F1 through F5 (FIG. 7). These fragments were assayed for their ability to interact with nuclear protein extract from rice suspension cells grown in the presence or absence of sucrose. In a gel mobility shift assay using F2 (which contains the TATCCA element) as a probe, two DNA-protein complexes (C1 and C2) were observed regardless of whether the nuclear extract was from cells grown in the presence ("+S") or absence ("−S") of sucrose. However, the band intensity was 5-fold higher for −S cells than for +S cells. C1 and C2 were competed out by 500 times excess of F2 itself or 150 times excess of F5, which encompasses F2.

In a gel mobility shift assay using F3 (which contains the G box and the 5' flanking sequence of the TATCCA element, a DNA-protein complex (C3) was observed regardless of whether the nuclear extract was from +S or −S cells. However, the band intensity was 4.5-fold higher for +S cells than for −S cells. C3 was competed out by 500 times excess of F3 itself or F4, or by 150 times excess of F5. Because F3 contains a 7-bp sequence TTTATTG (nucleotides −126 to −120), which is also present in F4 and F5 (nucleotides −99 to −93), it is believed that C3 was formed by binding of this 7-bp sequence by a component in the nuclear extract. F2 competed slightly for C3, probably because it contains a 4-bp sequence ATTG, which overlaps part of the 7-bp sequence (FIG. 7). These results demonstrate that nuclear proteins from rice suspension cells bind to the TATCCA element and its flanking sequences in a sequence-specific and sugar-dependent manner.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated DNA comprising two or more copies of a sugar-responsive enhancer of a cereal α-amylase gene.

2. The DNA of claim 1, wherein the cereal α-amylase gene is rice αAmy3.

3. The DNA of claim 2, wherein the sugar-responsive enhancer is SEQ ID NO:1.

4. The DNA of claim 2, wherein the sugar-responsive enhancer is SEQ ID NO:2.

5. The DNA of claim 2, wherein the sugar-responsive enhancer is SEQ ID NO:3.

* * * * *

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
      (A) LENGTH: 105 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO:1:

```
ATCCCGTCGC CTTGGAGACC GGGCCCCGAC GCGGCCGACG CGGCGCCTAC GTGGCCATGC        60

TTTATTGCCT TATCCATATC CACGCCATTT ATTGTGGTCG TCTCT                       105
```

(2) INFORMATION FOR SEQ ID NO:2:

(i) SEQUENCE CHARACTERISTICS:
        (A) LENGTH: 52 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:2:

```
GCCATGCTTT ATTGCCTTAT CCATATCCAC GCCATTTATT GTGGTCGTCT CT            52
```

(2) INFORMATION FOR SEQ ID NO:3:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

```
ATCCCGTCGC CTTGGAGACC GGGCCCCGAC GCGGCCGACG CGGCGCCTAC GTGGCCATGC    60

TTTAT                                                                65
```

(2) INFORMATION FOR SEQ ID NO:4:

(i) SEQUENCE CHARACTERISTICS:
        (A) LENGTH: 128 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:4:

```
TATATATGCC CCCCGACGTC GAGGTCATTC GCCACGAACA CATCGATCAT CCATCATCTA    60

CAAGAGATCG ATCAGTAGTG GTTAGCAGCA ACTCACTATC GAACACGGTT TCAGCTTACA   120

CAGATATG                                                            128
```

(2) INFORMATION FOR SEQ ID NO:5:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:5:

```
TATAAATACC TGACCAGACA CACCCAGGAG CTTCATCAAT CATCCATCTC CGAAGTGTGT    60

CTGCAGCATG CAGGTGCTGA ACACCATGGT GAACAAACAC TTCTTGTCC               109
```

(2) INFORMATION FOR SEQ ID NO:6:

(i) SEQUENCE CHARACTERISTICS:
        (A) LENGTH: 188 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:6:

```
TATAAATAGA GGCCAGTTCA GGCAATGCAA GAGCAGAGAA GCAGAGTACA GCAGGCAGCT      60

CTTCTTCTCT TTGCGAAGGT TGGCTACTTG GCCAGCCATT AGGAAACAAG TTAGTTTGGA     120

GAAGAAGCAG AGTTGAGACT GCATTTGCAT TGCTCTGTAG CCATGGGCAA GCACCATGTC     180

ACCCTGTG                                                              188
```

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:7:

```
GAGACCGGGC CCCGACGCGG CCGACGCGGC G                                     31
```

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:8:

```
TATCCATATC CA                                                          12
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:9:

```
GAGAGCTCGC GCCGCCTCGA TCGGCGCGGC G                                     31
```

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:10:

```
ATAACAAACT CCGG                                                        14
```

(2) INFORMATION FOR SEQ ID NO:11:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:11:

ATCCCGTCGC CTTACGAATT CATCCCCGAC GCGGCCGACG CGGCGCCTAC GTGGCCATGC    60

TTTATTGCCT TATCCATATC CACGCCATTT ATTGTGGTCG TCTCT    105

(2) INFORMATION FOR SEQ ID NO:12:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:12:

ATCCCGTCGC CTTGGAGACC GGGGTGAATT CATGCCGACG CGGCGCCTAC GTGGCCATGC    60

TTTATTGCCT TATCCATATC CACGCCATTT ATTGTGGTCG TCTCT    105

(2) INFORMATION FOR SEQ ID NO:13:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:13:

ATCCCGTCGC CTTGGAGACC GGGCCCCGAC GCGCTGAATT CATCGCCTAC GTGGCCATGC    60

TTTATTGCCT TATCCATATC CACGCCATTT ATTGTGGTCG TCTCT    105

(2) INFORMATION FOR SEQ ID NO:14:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:14:

ATCCCGTCGC CTTGGAGACC GGGCCCCGAC GCGGCCGACG CGGATGAATT CCAGCCATGC    60

TTTATTGCCT TATCCATATC CACGCCATTT ATTGTGGTCG TCTCT    105

(2) INFORMATION FOR SEQ ID NO:15:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:15:

ATCCCGTCGC CTTGGAGACC GGGCCCCGAC GCGGCCGACG CGGCGCCTAC GTGTAGAATT    60

CCGATTGCCT TATCCATATC CACGCCATTT ATTGTGGTCG TCTCT    105

(2) INFORMATION FOR SEQ ID NO:16:

(i) SEQUENCE CHARACTERISTICS:
        (A) LENGTH: 105 base pairs
        (B) TYPE: nucleic acid

```
        (C) STRANDEDNESS: double
        (D) TOPOLOGY: linear (ii) MOLECULE TYPE: DNA (xi) SEQUENCE DESCRIPTION: SEQ ID NO:16:

ATCCCGTCGC CTTGGAGACC GGGCCCCGAC GCGGCCGACG CGGCGCCTAC GTGGCCATGC      60

TTTGCGAATT CCGCCATATC CACGCCATTT ATTGTGGTCG TCTCT                    105

(2) INFORMATION FOR SEQ ID NO:17:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:17:

ATCCCGTCGC CTTGGAGACC GGGCCCCGAC GCGGCCGACG CGGCGCCTAC GTGGCCATGC      60

TTTATTGCCT TATTAGGAAT TCGGCCATTT ATTGTGGTCG TCTCT                    105

(2) INFORMATION FOR SEQ ID NO:18:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:18:

ATCCCGTCGC CTTGGAGACC GGGCCCCGAC GCGGCCGACG CGGCGCCTAC GTGGCCATGC      60

TTTATTGCCT TATCCATATC CACCTAGAAT TCGGTGGTCG TCTCT                    105

(2) INFORMATION FOR SEQ ID NO:19:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:19:

ATCCCGTCGC CTTGGAGACC GGGCCCCGAC GCGGCCGACG CGGCGCCTAC GTGGCCATGC      60

TTTATTGCCT TATCCATATC CACGCCATTT ATTACGAATT CAGCT                    105

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AGACCGGGCC CCGACGCGGC CGACGCGGCG                                      30

(2) INFORMATION FOR SEQ ID NO:21:
```

```
        (i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:21:

ATTGCCTTAT CCATATCCAC                                                    20

(2) INFORMATION FOR SEQ ID NO:22:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:22:

CCTACGTGGC CATGCTTTAT TGCCT                                              25

(2) INFORMATION FOR SEQ ID NO:23:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:23:

CGCCATTTAT TGTGGTCGTC TCT                                                23

(2) INFORMATION FOR SEQ ID NO:24:

(i) SEQUENCE CHARACTERISTICS:
             (A) LENGTH: 52 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:24:

GCCATGCTTT ATTGCCTTAT CCATATCCAC GCCATTTATT GTGGTCGTCT CT                 52

(2) INFORMATION FOR SEQ ID NO:25:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:25:

ATCTTCAACC ACCTGTGCTA                                                    20

(2) INFORMATION FOR SEQ ID NO:26:

(i) SEQUENCE CHARACTERISTICS:
             (A) LENGTH: 19 base pairs
             (B) TYPE: nucleic acid
             (C) STRANDEDNESS: single
             (D) TOPOLOGY: linear
```

(ii) MOLECULE TYPE: DNA (xi) SEQUENCE DESCRIPTION: SEQ ID NO:26:

GTGGATAGAA TTGCCATGT                                                    19

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AAATGGCTCG CCTTATCCA                                                    19

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

ATTTATTGTG GTCGTCTCT                                                    19

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

ATCTGTGTAA GCTGATTGGC A                                                 21

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

GTCGCCTTGG ATTGCCTTAT CCATA                                             25

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

```
GCCATGCTTT TCTCCTGATC ATTCT                                              25

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TGTGGTCGTC CGGTGTTCTA TATAT                                              25

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

ATCCCGTCGC CTTGGAGA                                                      18

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

AGAGACGACC ACAATAAAT                                                     19

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

ATAAAGCATG GCCACGTA                                                      18

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

CCTCCATCCA AGATGGTACC GGATAAGGCG                                         30

(2) INFORMATION FOR SEQ ID NO:37:
```

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

GCCTGAGGCA TCATCTAGAG GTCTCCTCCT                                    30

(2) INFORMATION FOR SEQ ID NO:38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

AAGGCGACGG TGCTATGCAT CGTGATCGCG                                    30

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CGGCCGCGTC TACAAGCTTA CTCCAAGGCG                                    30

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

TATTGCCTCT CGGATCCAGC CGCCATTTAT                                    30

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

CCCGGTCTCC AGAATTCACT GATGCGGCGG                                    30

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

CGCGTCGGGG ATGAATTCGT AAGGCGACGG                                    30

(2) INFORMATION FOR SEQ ID NO:43:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:43:

CCGCGTCGGC ATGAATTCAC CCCGGTCTCC                                    30

(2) INFORMATION FOR SEQ ID NO:44:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:44:

CACGTAGGCC ATGAATTCGT CGCCGTCGGG GG                                 32

(2) INFORMATION FOR SEQ ID NO:45:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:45:

AAAGCATGGC TGGAATTCAT CCGCGTCGGC                                    30

(2) INFORMATION FOR SEQ ID NO:46:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:46:

ATAAGGCAAT CGGAATTCTA CACGTAGGCG                                    30

(2) INFORMATION FOR SEQ ID NO:47:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:47:

```
GTGGATATGG CGGAATTCGC AAAGCATGGC                                               30

(2) INFORMATION FOR SEQ ID NO:48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

AATAAATGGC CGAATTCCTA ATAAGGCAAT                                               30

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

AGACGACCAC CGAATTCTAG GTGGATATGG                                               30

(2) INFORMATION FOR SEQ ID NO:50:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

TGATCCAGGA GCTGAATTCG TAATAAATGG C                                             31

(2) INFORMATION FOR SEQ ID NO:51:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

TCACTCGAGG CCATGCTTTA TTGCCTT                                                  27

(2) INFORMATION FOR SEQ ID NO:52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:52:

TCCATCGATG CCATGCTTTA TTGCCTT                                                  27

(2) INFORMATION FOR SEQ ID NO:53:
```

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

GCCATCGATA GAGACGACCA CAATAAA                                              27
```